(12) United States Patent
Hueller et al.

(10) Patent No.: US 9,365,881 B2
(45) Date of Patent: Jun. 14, 2016

(54) PROCESS FOR ANTIBODY G1 GLYCOFORM PRODUCTION

(71) Applicant: Hoffmann-La Roche Inc., Nutley, NJ (US)

(72) Inventors: Martina Hueller, Achmuehle (DE); Dietmar Reusch, Munich (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 263 days.

(21) Appl. No.: 14/348,822

(22) PCT Filed: Oct. 2, 2012

(86) PCT No.: PCT/EP2012/069394
§ 371 (c)(1),
(2) Date: Mar. 31, 2014

(87) PCT Pub. No.: WO2013/050335
PCT Pub. Date: Apr. 11, 2013

(65) Prior Publication Data
US 2014/0234899 A1    Aug. 21, 2014

(30) Foreign Application Priority Data
Oct. 5, 2011  (EP) .................................. 11184011

(51) Int. Cl.
*C07K 19/00* (2006.01)
*C07K 16/28* (2006.01)
*C07K 16/34* (2006.01)
*C12P 21/00* (2006.01)
*C07K 16/00* (2006.01)
*C07K 16/32* (2006.01)

(52) U.S. Cl.
CPC ............... *C12P 21/005* (2013.01); *C07K 16/00* (2013.01); *C07K 16/2803* (2013.01); *C07K 16/2866* (2013.01); *C07K 16/32* (2013.01); *C07K 2317/41* (2013.01)

(58) Field of Classification Search
None
See application file for complete search history.

(56) References Cited

U.S. PATENT DOCUMENTS

| | | | |
|---|---|---|---|
| 2004/0191256 A1 | 9/2004 | Raju | |
| 2008/0206808 A1* | 8/2008 | DeFrees | C12P 21/02 435/68.1 |
| 2009/0060921 A1 | 3/2009 | Dickey et al. | |
| 2011/0263828 A1* | 10/2011 | Wong | C07K 16/00 530/387.3 |

* cited by examiner

Primary Examiner — Daniel E Kolker
Assistant Examiner — James Rogers (57) ABSTRACT

The current invention comprises a method for producing an immunoglobulin or immunoglobulin fragment or immunoglobulin fusion with G1 glycostructure comprising incubating with a galactosyltransferase, a sialyltransferase, a beta-1,4-galactosidase and a sialidase, whereby the galactosyltransferase is added in more than one aliquot during the incubating.

7 Claims, 1 Drawing Sheet

PROCESS FOR ANTIBODY G1 GLYCOFORM PRODUCTION

This application is a 35 USC 371 of International Patent Application No. PCT/EP2012/069394 filed Oct. 2, 2012; which claims priority benefit to EP 11184011.2 filed Oct. 5, 2011, each of which are hereby incorporated herein by reference in their entireties.

The current invention is directed to a method for enzymatic downstream processing of recombinantly produced immunoglobulins. In more detail the current invention is directed to a method for producing an immunoglobulin with a G1 glycostructure in substantially pure form after an affinity chromatography step by an enzymatic treatment.

BACKGROUND OF THE INVENTION

Polypeptides obtained from eukaryotic cells are produced as glycosylated polypeptides. The glycostructures are attached to the amino acid backbone as post-translational enzymatic modification.

The glycosyltransferases are recognized as a functional family of estimated 250-300 different intracellular, membrane-bound enzymes that participate in the coordinate biosynthesis of the glycostructures of polypeptides, including glycoproteins, proteoglycans and glycolipids. The glycosyltransferases are classified into groups based on their nucleotide monosaccharide donor specificity. For example, the galactosyltransferases are the subset of glycosyltransferases that use UDP-galactose as the activated monosaccharide donor whereas the sialyltransferases use CMP-sialic acid and the fucosyltransferases use GDP-fucose (Shaper, N. L., et al., J. Mamm. Gland Biol. Neopl. 3 (1998) 315-324).

A method for clinical examination based on the structures of immunoglobulin G-linked oligosaccharides is reported in EP 0 698 793. In EP 1 878 747 glycoengineered antibodies are reported. Selective marking of immunoglobulin glycans is reported in WO 2007/071347. In WO 1997/016064 methods and compositions for the reduction of xenotransplantation rejection are reported. Antibody preparations with substantially homogeneous and non-sialilated glycostructures, such as G0 and G2, which are prepared by enzymatic treatment, expression under certain conditions, use of particular host cells, and contact with serum, are reported in WO 2007/024743.

In WO 2008/057634 polypeptides with enhanced anti-inflammatory and decreased cytotoxic properties and relating methods are reported. Proteolysis resistant antibody preparations are reported in WO 2007/024743.

SUMMARY OF THE INVENTION

It has been found that with the sequence of enzymatic steps as reported herein an immunoglobulin with a G1 glycostructure can be obtained in substantially pure form, i.e. with a purity of 90% or more, with a purity of 95% or more, or with a purity of 98% or more.

Therefore, herein is reported a method for producing an immunoglobulin or immunoglobulin fragment or a fusion polypeptide comprising a glycosylated immunoglobulin fragment with a G1 glycostructure in substantially pure form starting from a glycosylated immunoglobulin or a glycosylated immunoglobulin fragment or a fusion polypeptide comprising a glycosylated immunoglobulin fragment which is a mixture of G0, G1 and G2 glycostructures.

Also, herein is reported a method for producing an immunoglobulin or immunoglobulin fragment or a fusion polypeptide comprising a glycosylated immunoglobulin fragment with a G1 glycostructure in substantially pure form starting from a glycosylated immunoglobulin or a glycosylated immunoglobulin fragment or a fusion polypeptide comprising a glycosylated immunoglobulin fragment which has a G0 glycostructure.

Also, herein is reported a method for producing an immunoglobulin or immunoglobulin fragment or a fusion polypeptide comprising a glycosylated immunoglobulin fragment with a G1 glycostructure in substantially pure form starting from a glycosylated immunoglobulin or a glycosylated immunoglobulin fragment or a fusion polypeptide comprising a glycosylated immunoglobulin fragment which has a G2 glycostructure.

Thus, herein is reported a method for producing an immunoglobulin with a G1 glycostructure in substantially pure form or an immunoglobulin fragment with a G1 glycostructure in substantially pure form or a fusion polypeptide comprising a glycosylated immunoglobulin fragment with a G1 glycostructure in substantially pure form comprising the following steps in the following order:

providing an affinity chromatography column eluate containing an immunoglobulin or an immunoglobulin fragment or a fusion polypeptide, which is a mixture of a G0, G1 and G2 glycostructure, incubating the immunoglobulin or immunoglobulin fragment with a galactosyltransferase, incubating the immunoglobulin or immunoglobulin fragment or fusion polypeptide with a sialyltransferase, incubating the immunoglobulin or immunoglobulin fragment or fusion polypeptide with a beta-1,4-galactosidase or lactase, removing or inactivating the beta-1,4-galactoasidase or lactase, and incubating the immunoglobulin or immunoglobulin fragment or fusion polypeptide with a sialidase and thereby producing an immunoglobulin with a G1 glycostructure or an immunoglobulin fragment with a G1 glycostructure or a fusion polypeptide comprising a glycosylated immunoglobulin fragment with a G1 glycostructure in substantially pure form.

Thus, herein is reported a method for producing an immunoglobulin with a G1 glycostructure in substantially pure form or an immunoglobulin fragment with a G1 glycostructure in substantially pure form or a fusion polypeptide comprising a glycosylated immunoglobulin fragment with a G1 glycostructure in substantially pure form comprising the following steps in the following order:

providing an affinity chromatography column eluate containing an immunoglobulin, which has a G0 glycostructure, or an immunoglobulin fragment, which has a G0 glycostructure, or a fusion polypeptide, which has a G0 glycostructure, incubating the immunoglobulin or the immunoglobulin fragment or the fusion polypeptide with a galactosyltransferase, incubating the immunoglobulin or immunoglobulin fragment or the fusion polypeptide with a sialyltransferase, incubating the immunoglobulin or immunoglobulin fragment or the fusion polypeptide with a beta-1,4-galactosidase or lactase, removing or inactivating the beta-1,4-galactoasidase or lactase, and incubating the immunoglobulin or immunoglobulin fragment or the fusion polypeptide with a sialidase and thereby producing an immunoglobulin or immunoglobulin fragment or fusion polypeptide with a G1 glycostructure in substantially pure form.

Thus, herein is reported a method for producing an immunoglobulin with a G1 glycostructure in substantially pure form or an immunoglobulin fragment with a G1 glycostructure in substantially pure form or a fusion polypeptide comprising a glycosylated immunoglobulin fragment with a G1 glycostructure in substantially pure form comprising the following steps in the following order:

providing an affinity chromatography column eluate containing an immunoglobulin, which has a G2 glycostructure, or an immunoglobulin fragment, which has a G2 glycostructure, or a fusion polypeptide, which has a G2 glycostructure, incubating the immunoglobulin or immunoglobulin fragment or a fusion polypeptide with a sialyltransferase, incubating the immunoglobulin or immunoglobulin fragment or a fusion polypeptide with a beta-1,4-galactosidase or lactase, removing or inactivating the beta-1,4-galactoasidase or lactase, and incubating the immunoglobulin or immunoglobulin fragment or a fusion polypeptide with a sialidase and thereby producing an immunoglobulin or immunoglobulin fragment or fusion polypeptide with a G1 glycostructure in substantially pure form.

In one embodiment the galactosyltransferase is added in one to ten aliquots. In one embodiment the galactosyltransferase is added in two to seven aliquots. In one embodiment the galactosyltransferase is added in three to six aliquots. In one embodiment the galactosyltransferase is added in four or six aliquots.

In one embodiment the incubating with the galactosyltransferase is for about 30 hours to about 60 hours.

In one embodiment the first galactosyltransferase aliquot is added after zero to two hours of incubating. In one embodiment the first galactosyltransferase aliquot is added at the beginning of the incubating.

In one embodiment a galactosyltransferase aliquot is added five to twenty hours after the previous aliquot has been added. In one embodiment a galactosyltransferase aliquot is added six to twelve hours after the previous aliquot has been added. In one embodiment a galactosyltransferase aliquot is added eight to ten hours after the previous aliquot has been added.

In one embodiment the immunoglobulin or immunoglobulin fragment or fusion polypeptide is not purified prior to the incubation with sialyltransferase. In one embodiment the incubation with sialyltransferase is of the crude reaction mixture of the incubation with galactosyltransferase.

In one embodiment the removing is by column chromatography. In one embodiment the column chromatography is protein A affinity column chromatography.

In one embodiment the immunoglobulin or immunoglobulin fragment or fusion polypeptide is purified prior to the incubation with beta-1,4-galactgosidase.

In one embodiment the immunoglobulin or immunoglobulin fragment or fusion polypeptide is purified prior to the incubation with sialidase.

DETAILED DESCRIPTION OF THE INVENTION

Herein is reported that with the sequence of enzymatic steps of
i) galactosylation,
ii) sialidation,
iii) degalactosylation, and
iv) desialidation an immunoglobulin with a G1 glycostructure can be obtained in substantially pure form, i.e. with a purity of 90% or more, with a purity of 95% or more, or with a purity of 98% or more.

Especially the galactosylation has to be performed over a longer period of time of up to 60 hours, whereby the enzyme galactosyltransferase is added multiple times during this time period.

TABLE 1

Comparison of different number of aliquots used for processing an anti-HER2 antibody.

| number of galactosyltransferase aliquots | yield G2 glycoform |
| --- | --- |
| one, 19 hours incubation | approx. 40% |
| one, 48 hours incubation | approx. 60% |
| two, 21 hours incubation | approx. 65% |
| three, 30 hours incubation | approx. 75% |
| four, 48 hours incubation | approx. 90% |

TABLE 2

Comparison of different number of aliquots used for processing an anti-IL-1R antibody.

| number of galactosyltransferase aliquots | yield G2 glycoform |
| --- | --- |
| two, 21 hours incubation | approx. 80% |
| three, 28 hours incubation | approx. 95% |

Thus, in one embodiment the galactosyltransferase is added in one to ten aliquots. In one embodiment the galactosyltransferase is added in two to seven aliquots. In one embodiment the galactosyltransferase is added in three, or four, or five, or six aliquots.

In one embodiment the incubating with the galactosyltransferase is for about 30 hours to about 60 hours.

In one embodiment the first galactosyltransferase aliquot is added after zero to two hours of incubating. In one embodiment the first galactosyltransferase aliquot is added at the beginning of the incubating.

In one embodiment a galactosyltransferase aliquot is added five to twenty hours after the previous aliquot has been added. In one embodiment a galactosyltransferase aliquot is added six to twelve hours after the previous aliquot has been added. In one embodiment a galactosyltransferase aliquot is added eight to ten hours after the previous aliquot has been added.

Herein is reported a method for producing an immunoglobulin or immunoglobulin fragment with a G1 glycostructure in substantially pure form comprising the following steps:

providing an affinity chromatography column eluate containing the immunoglobulin or immunoglobulin fragment, incubating the affinity chromatography column eluate with a galactosyltransferase, incubating the galactosyltransferase reaction product with a sialyltransferase, incubating the sialyltransferase reaction product with a beta-1,4-galactosidase, removing or inactivating the beta-1,4-galactoasidase, and incubating the beta-1,4-galactosidase reaction product in which the beta-1,4-galactosidase has been removed or inactivated with a sialidase.

The beta-1,4-galactosidase or its activity, respectively, has to be removed/inactivated prior to the addition of the sialidase in order to obtain the G1 glycostructure. In the presence of catalytically active beta-1,4-galactosidase the intermediate reaction product would be transformed to the G0 glycostructure.

In one embodiment the galactosyltransferase is a beta-1,4-galactosyltransferase. In one embodiment the galactosyltransferase is beta-1,4-galactosyltransferase from bovine milk.

Human immunoglobulins are mainly glycosylated at the asparagine residue at about position 297 (Asn297) of the heavy chain CH2 domain or in the FAB region with a more or less fucosylated biantennary complex oligosaccharide (immunoglobulin amino acid residue numbering according to Kabat, see below). The biantennary glycostructure can be terminated by up to two consecutive galactose (Gal) residues in each arm. The arms are denoted (1,6) and (1,3) according to the glycoside bond to the central mannose residue. The glycostructure denoted as G0 comprises no galactose residue. The glycostructure denoted as G1 contains one or more galactose residues in one arm. The glycostructure denoted as G2 contains one or more galactose residues in each arm (Raju, T. S., Bioprocess Int. 1 (2003) 44-53). Human constant heavy chain regions are reported in detail by Kabat, E. A., et al., Sequences of Proteins of Immunological Interest, 5th ed., Public Health Service, National Institutes of Health, Bethesda, Md. (1991), and by Brueggemann, M., et al., J. Exp. Med. 166 (1987) 1351-1361; Love, T. W., et al., Methods Enzymol. 178 (1989) 515-527. CHO type glycosylation of immunoglobulin Fc parts is e.g. described by Routier, F. H., Glycoconjugate J. 14 (1997) 201-207.

The term "immunoglobulin" denotes and encompasses the various forms of immunoglobulins such as human immunoglobulins, humanized immunoglobulins, chimeric immunoglobulins, or T-cell antigen depleted immunoglobulins (see e.g. WO 98/33523, WO 98/52976, and WO 00/34317). In one embodiment the antibody in the methods as reported herein is a human or humanized antibody. Genetic engineering of immunoglobulins is e.g. described in Morrison, S. L., et al., Proc. Natl. Acad. Sci. USA 81 (1984) 6851-6855; U.S. Pat. No. 5,202,238 and U.S. Pat. No. 5,204,244; Riechmann, L., et al., Nature 332 (1988) 323-327; Neuberger, M. S., et al., Nature 314 (1985) 268-270; Lonberg, N., Nat. Biotechnol. 23 (2005) 1117-1125.

An immunoglobulin in general comprises two so called full length light chain polypeptides (light chain) and two so called full length heavy chain polypeptides (heavy chain). Each of the full length heavy and light chain polypeptides contains a variable domain (variable region) (generally the amino terminal portion of the full length polypeptide chain) comprising binding regions which interact with an antigen. Each of the full length heavy and light chain polypeptides comprises a constant region (generally the carboxyl terminal portion). The constant region of the full length heavy chain mediates the binding of the immunoglobulin i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q). The variable domain of a full length immunoglobulin's light or heavy chain in turn comprises different segments, i.e. four framework regions (FR) and three hypervariable regions (CDR). A "full length immunoglobulin heavy chain" is a polypeptide consisting in N-terminal to C-terminal direction of an immunoglobulin heavy chain variable domain (VH), an immunoglobulin constant domain 1 (CH1), an immunoglobulin hinge region, an immunoglobulin constant domain 2 (CH2), an immunoglobulin constant domain 3 (CH3), and optionally an immunoglobulin constant domain 4 (CH4) in case of an immunoglobulin of the subclass IgE. A "full length immunoglobulin light chain" is a polypeptide consisting in N-terminal to C-terminal direction of an immunoglobulin light chain variable domain (VL), and an immunoglobulin light chain constant domain (CL). The full length immunoglobulin chains a linked together via interpolypeptide disulfide bonds between the CL-domain and the CH1 domain and between the hinge regions of the full length immunoglobulin heavy chains.

The term "immunoglobulin fragment" denotes within this application a polypeptide comprising at least the CH2 domain and the CH3 domain of a full length immunoglobulin heavy chain. An immunoglobulin fragment may also comprise additional non-immunoglobulin derived amino acid sequences.

Is has been reported in recent years that the glycosylation pattern of immunoglobulins, i.e. the saccharide composition and multitude of attached glycostructures, has a strong influence on the biological properties (see e.g. Jefferis, R., Biotechnol. Prog. 21 (2005) 11-16). Immunoglobulins produced by mammalian cells contain 2-3% by mass oligosaccharides (Taniguchi, T., et al., Biochem. 24 (1985) 5551-5557). This is equivalent e.g. in an immunoglobulin of class G (IgG) to 2.3 oligosaccharide residues in an IgG of mouse origin (Mizuochi, T., et al., Arch. Biochem. Biophys. 257 (1987) 387-394) and to 2.8 oligosaccharide residues in an IgG of human origin (Parekh, R. B., et al., Nature 316 (1985) 452-457), whereof generally two are located in the Fc-region at $Asn^{297}$ and the remaining in the variable region (Saba, J. A., et al., Anal. Biochem. 305 (2002) 16-31).

The term "glycostructure" as used within this application denotes a single, defined N- or O-linked oligosaccharide at a specified amino acid residue. Thus, the term "immunoglobulin with a G1 glycostructure" denotes an immunoglobulin comprising at the asparagine amino acid residue at about amino acid position 297 according to the Kabat numbering scheme or in the FAB region a biantennary oligosaccharide comprising only one terminal galactose residue at the non-reducing ends of the oligosaccharide. The term "oligosaccharide" as used within this application denotes a polymeric saccharide comprising two or more covalently linked monosaccharide units.

For the notation of the different N- or O-linked oligosaccharides in the current invention the individual sugar residues are listed from the non-reducing end to the reducing end of the oligosaccharide molecule. The longest sugar chain was chosen as basic chain for the notation. The reducing end of an N- or O-linked oligosaccharide is the monosaccharide residue, which is directly bound to the amino acid of the amino acid backbone of the immunoglobulin, whereas the end of an N- or O-linked oligosaccharide, which is located at the opposite terminus as the reducing end of the basic chain, is termed non-reducing end.

The term "affinity chromatography" as used within this application denotes a chromatography method which employs an "affinity chromatography material". In an affinity chromatography polypeptides are separated based on their biological activity or chemical structure depending on the formation of electrostatic interactions, hydrophobic bonds, and/or hydrogen bonds to the chromatographical functional groups of the chromatography material. To recover the specifically bound polypeptide from the affinity chromatography material either a competitor ligand can be added or the chromatography conditions, such as pH value, polarity or ionic strength of the buffer, can be changed. Exemplary "affinity chromatography materials" are metal chelating chromatography materials such as Ni(II)-NTA or Cu(II)-NTA, or immunoglobulin affinity chromatography materials such as in one embodiment of the methods as reported herein chromatography materials comprising thereto covalently linked protein A or protein G, or enzyme binding affinity chromatography materials such as chromatography materials comprising thereto covalently bound enzyme substrate analogues, enzyme cofactors, or enzyme inhibitors as chromatographical functional group, or lectin binding chromatography materials such as chromatography materials comprising thereto covalently linked polysaccharides, cell surface receptors, glycoproteins, or intact cells as chromatographical functional group.

The term "defined glycostructure" denotes within this application a glycostructure in which the monosaccharide residue at the non-reducing ends of the glycostructure is of a specific kind. The term "defined glycostructure" denotes within this application a glycostructure in which the monosaccharide residue at the non-reducing end of glycostructures are defined and of a specific kind.

The term "applying to" and grammatical equivalents thereof as used within this application denotes a partial step of a purification method in which a solution containing a substance of interest is brought in contact with a stationary phase. The solution containing the substance of interest to be purified passes through the stationary phase providing for an interaction between the stationary phase and the substances in solution. Depending on the conditions, such as e.g. pH, conductivity, salt concentration, temperature, and/or flow rate, some substances of the solution are bound to the stationary phase and therewith are removed from the solution. Other substances remain in solution. The substances remaining in solution can be found in the flow-through. The "flow-through" denotes the solution obtained after the passage of the chromatographic device, which may either be the applied solution containing the substance of interest or the buffer, which is used to flush the column or to cause elution of one or more substances bound to the stationary phase. The substance of interest can be recovered from the solution after the purification step by methods familiar to a person of skill in the art, such as e.g. precipitation, salting out, ultrafiltration, diafiltration, lyophilization, affinity chromatography, or solvent volume reduction to obtain the substance in substantially homogeneous form.

An immunoglobulin or immunoglobulin fragment whose glycostructure can be modified in the methods as reported herein can be produced by recombinant means. Methods for recombinant production are widely known in the state of the art and comprise protein expression in eukaryotic cells with subsequent isolation of the immunoglobulin or immunoglobulin fragment and purification to a pharmaceutically acceptable purity. For the expression of the immunoglobulin or immunoglobulin fragment either a hybridoma cell or a eukaryotic cell, in which one or more nucleic acids encoding the immunoglobulin or immunoglobulin fragment have been introduced, is used. In one embodiment the eukaryotic cells is selected from CHO cells, NS0 cells, SP2/0 cells, HEK 293 cells, COS cells, PER.C6 cells, BHK cells, rabbit cells, or sheep cells. In another embodiment the eukaryotic cell is selected from CHO cells, HEK cells, or rabbit cells. After expression the immunoglobulin or immunoglobulin fragment is recovered from the cells (from the supernatant or from the cells after lysis). General methods for recombinant production of immunoglobulins are well-known in the state of the art and reported, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-160; Werner, R. G., Drug Res. 48 (1998) 870-880.

Purification of immunoglobulins or immunoglobulin fragments can be performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art (see e.g. Ausubel, F. M, et al. (eds.), Current Protocols in Molecular Biology, John Wiley & Sons, Inc., New York (2005)). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis), as well as combinations thereof, such as affinity chromatography with microbial proteins, cation exchange chromatography and anion exchange chromatography (see e.g. Vijayalakshmi, M. A., Appl. Biochem. Biotech. 75 (1998) 93-102).

The glycostructure of a recombinantly produced immunoglobulin or immunoglobulin fragment will be determined by the employed cell line and the employed cultivation conditions. With conventional downstream processing techniques selective removal of specific glycostructures is not possible.

With the methods as reported herein an immunoglobulin or immunoglobulin fragment with defined glycostructure can be obtained in downstream processing. It has been found that for producing an immunoglobulin or immunoglobulin FAB fragment with a G1 glycostructure a sequential incubation with i) a galactosyltransferase, ii) a sialyltransferase, iii) a beta-1,4-galactosidase, and iv) a sialidase has to be performed in order to obtain the immunoglobulin or immunoglobulin FAB fragment with a G1 glycostructure in substantially pure form.

The method as reported herein allows for the production of an immunoglobulin or immunoglobulin fragment with G1 glycostructure whereby
  the need to obtain/select/use a cell line that produces a defined glycostructure is obsolete,
  the product quality due to the additional incubation steps of the immunoglobulin or immunoglobulin fragment compared to a method without the additional incubation steps is not changed,
  an immunoglobulin or immunoglobulin fragment with a defined glycostructure is produced during the downstream processing, i.e. after the expression is finished in vitro,
  the immunoglobulin with defined glycostructure is provided with improved yield as no immunoglobulin with unwanted glycostructure is removed but all immunoglobulin is enzymatically converted to a defined glycostructure.

Thus, one aspect as reported herein is a method for producing an immunoglobulin or immunoglobulin fragment with G1 glycostructure comprising the following step:
  incubating with a beta-1,4-galactosyltransferase,
  incubating with a sialyltransferase,
  incubating with a beta-1,4-galactosidase,
  inactivating or removing the beta-1,4-galactosidase, and
  incubating with a sialidase.

In one embodiment the galactosyltransferase is added in one to ten aliquots. In one embodiment the galactosyltransferase is added in two to seven aliquots. In one embodiment the galactosyltransferase is added in three, or four, or five, or six aliquots.

In one embodiment the incubating with the galactosyltransferase is for about 30 hours to about 60 hours.

In one embodiment the first galactosyltransferase aliquot is added after zero to two hours of incubating. In one embodiment the first galactosyltransferase aliquot is added at the beginning of the incubating.

In one embodiment a galactosyltransferase aliquot is added five to twenty hours after the previous aliquot has been added. In one embodiment a galactosyltransferase aliquot is added six to twelve hours after the previous aliquot has been added. In one embodiment a galactosyltransferase aliquot is added eight to ten hours after the previous aliquot has been added.

Thus, one aspect as reported herein is a method for producing an immunoglobulin or immunoglobulin fragment with G1 glycostructure comprising the following steps:
  providing an affinity chromatography column eluate containing the immunoglobulin or immunoglobulin fragment,
  incubating the affinity chromatography column eluate with a galactosyltransferase,
  incubating the galactosyltransferase reaction product with a sialyltransferase,
  incubating the sialyltransferase reaction product with a beta-1,4-galactosidase,
  removing or inactivating the beta-1,4-galactosidase, and
  incubating the beta-1,4-galactosidase reaction product, in which the beta-1,4-galactosidase activity had been removed or inactivated, with a sialidase.

It has been found that the galactosyltransferase has to be added in more than one aliquot during the incubation time. In one embodiment the galactosyltransferase is added in one to ten aliquots. In one embodiment the galactosyltransferase is added in two to seven aliquots. In one embodiment the galactosyltransferase is added in three, or four, or five, or six aliquots.

In one embodiment the incubating with the galactosyltransferase is for about 30 hours to about 60 hours.

In one embodiment the first galactosyltransferase aliquot is added after zero to two hours of incubating. In one embodiment the first galactosyltransferase aliquot is added at the beginning of the incubating.

In one embodiment a galactosyltransferase aliquot is added five to twenty hours after the previous aliquot has been added. In one embodiment a galactosyltransferase aliquot is added six to twelve hours after the previous aliquot has been added. In one embodiment a galactosyltransferase aliquot is added eight to ten hours after the previous aliquot has been added.

A further aspect as reported herein is a method for producing an immunoglobulin or immunoglobulin fragment or immunoglobulin fusion with G1 glycostructure comprising the following steps:
  cultivating a cell comprising a nucleic acid encoding the immunoglobulin or immunoglobulin fragment or immunoglobulin fusion,
  recovering the immunoglobulin or immunoglobulin fragment or immunoglobulin fusion from the cell or the cultivation medium,
  applying the recovered immunoglobulin or immunoglobulin fragment or immunoglobulin fusion to a protein A chromatography material and recovering the immunoglobulin from the protein A chromatography material by eluting the immunoglobulin or immunoglobulin fragment or immunoglobulin fusion from the protein A chromatography material,
  modifying the immunoglobulin or immunoglobulin fragment or immunoglobulin fusion contained in the affinity chromatography column eluate by
    a) incubating the affinity chromatography column eluate with a galactosyltransferase,
    b) incubating the galactosyltransferase reaction product with a sialyltransferase,
    c) incubating the sialyltransferase reaction product with a beta-1,4-galactosidase,
    d) removing or inactivating the beta-1,4-galactosidase,
    e) incubating the beta-1,4-galactosidase reaction product, in which the beta-1,4-galactosidase activity had been removed or inactivated, with a sialidase,
  applying the enzymatically modified affinity chromatography column eluate to a protein A chromatography material and recovering the immunoglobulin or immunoglobulin fragment or immunoglobulin fusion from the protein A chromatography material and thereby producing an immunoglobulin or immunoglobulin fragment or immunoglobulin fusion with G1 glycostructure.

For the purification of immunoglobulins or immunoglobulin fragments, which have been produced e.g. by cell cultivation methods, generally a combination of different chromatography steps can be employed. Normally a protein A affinity chromatography can be followed by one or two additional separation steps. In one embodiment the additional chromatography steps are a cation and an anion exchange chromatography step or vice versa. The final purification step is a so called "polishing step" for the removal of trace impurities and contaminants like aggregated immunoglobulins, residual HCP (host cell protein), DNA (host cell nucleic acid), viruses, or endotoxins. In one embodiment the final purification step is an anion exchange chromatography in flow-through mode.

General chromatographic methods and their use are known to a person skilled in the art. See for example, Heftmann, E. (ed.), Chromatography, 5$^{th}$ edition, Part A: Fundamentals and Techniques, Elsevier Science Publishing Company, New York (1992); Deyl, Z. (ed.), Advanced Chromatographic and Electromigration Methods in Biosciences, Elsevier Science BV, Amsterdam, The Netherlands (1998); Poole, C. F., and Poole, S. K., Chromatography Today, Elsevier Science Publishing Company, New York (1991); Scopes, Protein Purification: Principles and Practice (1982); Sambrook, J., et al. (eds.), Molecular Cloning: A Laboratory Manual, Second Edition, Cold Spring Harbor Laboratory Press, Cold Spring Harbor, N.Y. (1989); or Ausubel, F. M., et al. (eds.), Current Protocols in Molecular Biology, John Wiley & Sons, Inc., New York (2005).

In one embodiment the galactosyltransferase is beta-1,4-galactosylatranferase. In one embodiment the galactosyltransferase is beta-1,4-galactosylatranferase from bovine milk.

In one embodiment the sialyltransferase is alpha-2,6-sialyltransferase. In one embodiment the sialyltransferase is human alpha-2,6-sialyltransferase.

In one embodiment the galactosidase is a beta-1,4-galactosidase. In one embodiment the galactosidase is a beta-1-3,4-galactosidase. In one embodiment the galactosidase is beta-1,4-galactosidase from bovine testis.

In one embodiment the sialidase is a neuraminidase. In one embodiment the neuraminidase is a bacterial neuraminidase. In one embodiment the neuraminidase is alpha-2-3,6,8,9- neuraminidase. In one embodiment the neuraminidase is from *Arthrobacter ureafaciens*.

The following examples, figures and sequences are provided to aid the understanding of the present invention, the true scope of which is set forth in the appended claims. It is understood that modifications can be made in the procedures set forth without departing from the spirit of the invention.

EXAMPLES

Figure 1:
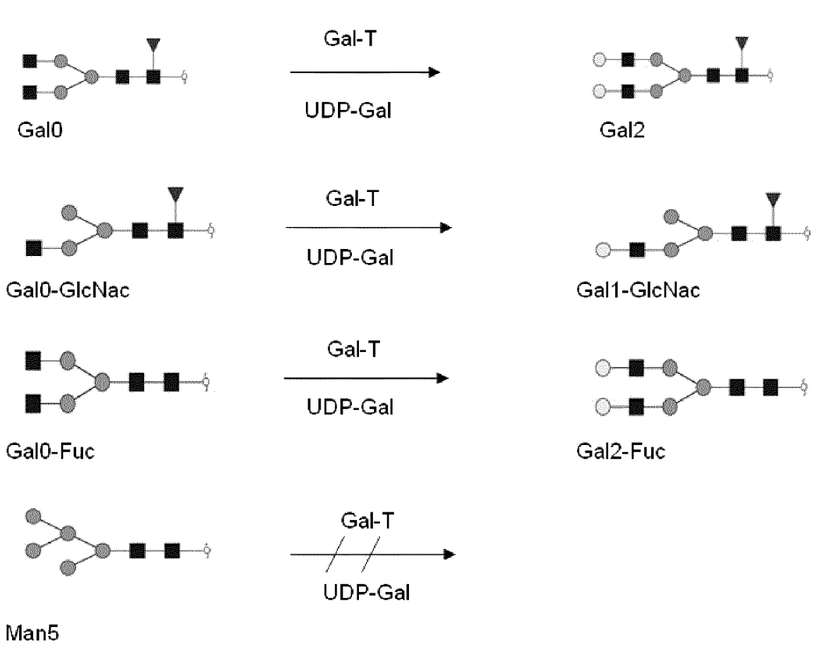
FIG. 1 Scheme of the production method as reported herein.

Analytics can be done between the different steps of synthesis or after the complete synthesis. If one or more of the intermediates are to be produced the synthesis can be finished after each of the steps.

The method as reported herein is exemplified in the following with different antibodies: anti-CD 19 antibody as reported in WO 2011/147834, anti-CCR5 antibody as reported in WO 2006/103100, anti-HER2 antibody as reported in WO 99/57134, anti-IL1R antibody as reported in WO 2005/023872.

Materials and Methods

Centrifuge tubes Membrane 10,000 MWCO e.g. Vivaspin 500 VS0102 Sartorius or Vivaspin 6 VS0601 Sartorius (for bigger amounts of antibodies)

ESMS-Analysis:
Material:
Guanidinium-Hydrochloride (e.g. Pierce, Cat-Nr. 24110)
TCEP (Tris-2-Carboxyethyl-Phosphin-Hydrochlorid) (e.g. Pierce, Cat-Nr. 20490)
NAP5-Gelfiltration columns Sephadex G-25 (e.g. GE Healthcare, Cat-Nr. 17-0853-02)
Formic acid min. 98% (e.g. Roth Cat-Nr. 4724.1)
Acetonitrile (e.g. Baker, Cat-Nr. 9017)
Ultrapure water (e.g. Baker)
ESI-MS Method:
The antibody was denatured, reduced with TCEP and the buffer was exchanged to electrospray-medium. Thereafter the antibody was measured with an electrospray-mass spectrophotometer. The m/z values of the light chain and different glycosylated heavy chains were determined.
Sample Preparation (Exemplary Method):
The glycerin was removed by washing with water. The samples were transferred to the prepared Vivaspin centrifuge tubes and filled with ultrapure water to about 100 µl volume. The samples were centrifuged at about 10 rpm, the filtrate was discarded. Thereafter the samples were cleaned at least two times each with about 100 µl ultrapure water. The residual liquid was transferred into a reaction tube and filled with ultrapure water to about 200 µl volume/1000 µg antibody.

For higher amounts of antibody (more than ca. 3000 µg antibody) the procedure can be adapted on Vivaspin centrifuge tubes Vivaspin 6 VS0601.

Reduction:
150 µg antibody was brought to a final volume of 200 µl with denaturation buffer (6 M guanidinium-hydrochloride). About 30 µl TCEP-solution (28.6 mg TCEP in 1 ml denaturation buffer) were added. The samples were incubated for about one hour at about 37° C.

Buffer Exchange:
The NAP5-Gelfiltration columns were equilibrated with 10 ml electrospray-medium (1% formic acid in 20% acetonitrile). Thereafter about 200 µl of the sample were transferred to the column. After complete draining about 650 µl electrospray-medium were applied to the column. The antibody was eluted with about 250 µl electrospray-medium.

ESMS-Analysis:
The reduced samples were analyzed for at least one minute between about 700 m/z to about 2200 m/z
MALDI-MS-Analysis:
Material:
N-Glycosidase F (e.g. Roche Diagnostics GmbH, Cat-Nr. 1 365 193)
Cation exchanger AG 50W-X8 Resin (e.g. BioRad, Cat-Nr. 142-1441)
Spin-Chromatography-Columns
DHB MALDI Matrix (e.g. Mass Prep)
Method:
The N-glycosidic oligosaccharides were cleaved from the antibody by N-glycosidase F digestion. The obtained oligosaccharides were analyzed by means of MALDI-TOF mass spectrometry after isolation of the protein.
Enzymatic Digest:
Two hundred fifty microgram of the purified samples were digested with 5 µl N-glycosidase F solution for about 18 hours at about 37° C.
Purification:
The digested samples were centrifuged by means of Vivaspin centrifuge tubes. The oligosaccharides were separated from the protein. The oligosaccharides were purified by means of a cation exchanger.
Analysis:
One microliter matrix was mixed with 1 µl sample and transferred onto the target. The samples were measured between 800 m/z and 2500 m/z.
HPAEC-Analysis:
Material:
Sodium dihydrogenphosphate-Monohydrate (e.g. Merck, Cat-Nr. 6346)
NAP5-Gelfiltration columns Sephadex G-25 (e.g. GE Healthcare, Cat-Nr. 17-0853-02)
Sodium hydroxide 50% (e.g. Baker, Cat-Nr. 7067)
Sodium acetate anhydrous (e.g. Merck, Cat-Nr. 6264)
N-Glycosidase F (e.g. Roche Diagnostics GmbH, Cat-Nr. 1 365 193)
Helium (purity min 4.6)
Ultrapure water (e.g. Baker, Cat-Nr. 4218)
HPAEC Method:
The N-glycosidic oligosaccharide-chains were separated from the antibody by cleavage with N-Glycosidase F. The obtained oligosaccharides were separated by means of an anion exchange chromatography (HPAEC) after isolating the protein.
Solutions:
phosphate buffer 10 mM, pH 7.2
N-Glycosidase F at a concentration of 1 U/µl
eluent A (0.05 mol/l NaOH); the solution is aerated with helium during preparation an analysis
eluent B (0.05 mol/l NaOH+0.2 mol/l Na-acetate); the solution is aerated with helium during preparation and analysis
Buffer Exchange:
The NAP5-Gelfiltration column was equilibrated with 10 ml phosphate buffer. Thereafter about 400 µg of the sample were transferred to the column. After complete draining 750 µl phosphate buffer were applied to the column. The antibody was eluted with 450 µl phosphate buffer. The samples were concentrated in prepared Vivaspin-centrifuge tubes to a volume of less than 100 µl.
Enzymatic Digest:
Two microliters of the N-glycosidase F solution (2 U) were added to the concentrated eluate. The eluate was incubated for about 16 h at about 37° C.
Purification:
The solution was transferred completely to the prepared Vivaspin centrifuge tube. About 50 µl ultrapure water were added and the solution was centrifuged at about 5000×g. Thereafter the samples were washed with about 50 μl ultrapure water. The centrifugate was transferred to a cup and filled up with ultrapure water to a final volume of about 140 μl.

Analysis:
Fifty microliter of the sample were injected to the HPLC-column (column temperature: 30° C.)
Gradient:
Gradient for non-sialidated samples:
Flow: 0.5 ml/min

| min | % B |
|---|---|
| 0 | 0 |
| 2 | 0 |
| 15 | 2 |
| 20 | 2 |
| 35 | 3 |
| 37 | 100 |
| 42 | 100 |
| 44 | 0 |
| 55 | 0 |

Gradient for sialidated samples:
Flow: 0.5 ml/min

| min | % B |
|---|---|
| 0 | 0 |
| 2 | 0 |
| 15 | 2 |
| 20 | 2 |
| 35 | 3 |
| 55 | 50 |
| 57 | 100 |
| 62 | 100 |
| 64 | 0 |
| 75 | 0 |

Example 1

Galactosylation

Materials:
Manganese(II)chloride >99%, MW 125.84 g/mol (Sigma-Aldrich, Cat-Nr. 244589-10G)
MES-buffer, MW 213.9 g/mol (Roche Diagnostics GmbH, Cat-Nr. 10073571001)
UDP-Galactose, disodium salt, MW 610.27 g/mol (Roche Diagnostics GmbH)
NaOH 50% (Sigma Aldrich, Cat-Nr. 41,541-3)
Galactosyltransferase β-1,4 (Fluka, from bovine milk, Cat-Nr. 48279 WA 10530; 1.13 U/mg)
Ultrapure water (Baker)
Sequence of steps:
addition of reaction buffer
addition of galactosyltransferase (3 to 6 times)
incubation Solutions:
Reaction buffer (for 1 l): $MnCl_2$ (2.52 g), UDP-Galactose (6.10 g), MES-Puffer (21.33 g)
The reagents are weighted in and dissolved in 950 ml ultrapure water. After that the pH-value of the solution is adjusted to pH 6.5 to pH 8.5 with 50% NaOH.
The buffer coagulates and has to be mixed just before use.
Galactosyltransferase-Solution:
0.887 mg (=1.0 U) galactosyltransferase were dissolved in 101.2 μl Reaction buffer.
Sample Preparation:
To about 1000 μg antibody were added about 150 μl Reaction buffer. The samples were diluted in ultrapure water to 300 μl liquid/1000 μg antibody.
Enzymatic Reaction:
To 1000 μg of the antibody 2.5 μl of the galactosyltransferase (0.025 U) was added. The addition of the enzyme was in three to six aliquots over a time period of 30 hours to 60 hours. The temperature was kept at 30° C. to 34° C.
Results:
After the incubation with the enzyme the enzymatically modified antibody was obtained with a yield as depicted in the following table.

TABLE

| antibody before reaction | antibody after reaction | G2 [%] | other, non-convertible glycostructures |
|---|---|---|---|
| anti-CD19 antibody | anti-CD19 antibody G2 glycostructure | >80 | Mannose 5 (approx. 8%) G1-GlcNac (approx. 5%) G2-Fuc |
| anti-CCR5 antibody | anti-CCR5 antibody G2 glycostructure | >65 | Mannose 5 (approx. 20%) G2-Fuc (approx. 8%) G1-GlcNac (approx. 4%) |
| anti-HER2 antibody | anti-HER2 antibody G2 glycostructure | >80 | G1-GlcNac (approx. 10%) G2-Fuc (approx. 4%) |
| anti-IL1R antibody | anti-IL1R antibody G2 glycostructure | >97 | G1-GlcNac (approx. 2%) |

Example 2

Sialidation

Materials:
CMP-Sialic acid M=658.4 g/mol (Sigma-Aldrich, Cat-Nr. C8271-1MG)
Sialyltransferase α-2,6 (Calbiochem, Cat-Nr. 566223)
Sequence of Steps:
addition of sialyltransferase
addition of CMP-sialic acid
incubation
Enzymatic Reaction:
For about 1000 μg antibody about 9 μl Sialyltransferase (12.9 mU) and 0.25 mg (=0.38 μmol) CMP-sialic acid were added. The samples were incubated at 30° C. to 37° C. for about 2 hours.
Results:
After the incubation with the enzyme the enzymatically modified antibody was obtained with a yield as depicted in the following table.

TABLE

| antibody before reaction | antibody after reaction | G2_1SA [%] | G2_2SA / Man5 [%] | other, non-convertible glycostructures |
|---|---|---|---|---|
| anti-CD19 antibody G2 glycostructure | anti-CD19 antibody G2-NANA glycostructure | >75 | approx. 10 | G1-GlcNac (+/− 1SA) |

TABLE-continued

| antibody before reaction | antibody after reaction | G2_1SA [%] | G2_2SA / Man5 [%] | other, non-convertible glycostructures |
|---|---|---|---|---|
| anti-CCR5 antibody G2 glycostructure | anti-CCR5 antibody G2-NANA glycostructure | >65 | approx. 20 | G2-Fuc 1SA, G1-GlcNac (+/− 1SA) |
| anti-HER2 antibody G2 glycostructure | anti-HER2 antibody G2-NANA glycostructure | >80 | <3 | G1-GlcNac approx. 10 %(+/− 1SA), G2-Fuc 1SA, G2 |
| anti-IL1R antibody G2 glycostructure | anti-IL1R antibody G2-NANA glycostructure | 80-90 | 10-15 | G1-GlcNac (+/− SA) |

Example 3

Degalactosylation

Materials:
β-1,4 Galactosidase (Glyco, Cat-Nr. GKX-5014, 200 mU)
Sequence of Steps:
purification
addition of β-1,4 galactosidase
incubation
Sample Preparation:
The samples were transferred to the prepared Vivaspin centrifuge tubes and ultrapure water was filled to approx. 100 µl total volume. The samples were centrifuged at ca. 10 rpm, the filtrate was discarded. Thereafter the samples were washed at least two times each with ca. 100 µl ultrapure water. The residual liquid was transferred into a reaction tube and filled with ultrapure water to about 200 µl volume/1000 µg antibody. Glycerin was removed by washing with water.

For higher amounts of antibody (more than about 3000 µg antibody) the procedure can be adapted on Vivaspin centrifuge tubes Vivaspin 6 VS0601.

Enzymatic Reaction:
For about 1000 µg antibody about 30 µl (60 mU) β-galactosidase solution were added. The samples were incubated for about 18 hours at about 37° C.

Results:
After the incubation with the enzyme the enzymatically modified antibody was obtained with a yield as depicted in the following table.

TABLE

| antibody before reaction | antibody after reaction | G1_1SA [%] | other, non-convertible glycostructures |
|---|---|---|---|
| anti-CD19 antibody G2-NANA glycostructure | anti-CD19 antibody G1-NANA glycostructure | >75 | Mannose 5 G1_1SA-Fuc G2_2SA G1(1SA)-GlcNac |
| anti-CCR5 antibody G2-NANA glycostructure | anti-CCR5 antibody G1-NANA glycostructure | >65 | Mannose 5 (approx. 20%) G1-Fuc_1SA G1-GlcNac (+/− 1SA) |
| anti-HER2 antibody G2-NANA glycostructure | anti-HER2 antibody G1-NANA glycostructure | >80 | G1-GlcNac (approx. 10%) (+/− 1SA) G1-Fuc_1SA G0 (from G2) |
| anti-IL1R antibody G2-NANA glycostructure | anti-IL1R antibody G1-NANA glycostructure | 80-90 | 10-15% G2_2SA |

Example 4

Desialidation

Materials:
MabSelectSuRe Column (Media Scout Mini Column, Atoll, Cat-Nr. 00101050408R)
Tris(hydroxymethyl) aminomethane (Merck, Cat-Nr. 1.08382)
NaCl (Merck, Cat-Nr. 1.06404)
Tri-sodium-citrate dihydrate (Merck, Cat-Nr. 1.06448)
NaOH 50% (Sigma Aldrich, Cat-Nr. 41,541-3)
Neuraminidase (Roche, Cat-Nr. 10 269 611 001, 1U)
Sequence of Steps:
purification (removing/inactivation of β-galactosidase)
addition of sialidase
incubation
Sample Preparation:
First the β-galactosidase was deactivated/removed to prevent the formation of G0 species.

The β-galactosidase was removed by chromatography with MabSelectSuRe columns (manually or automated using a Tecan Roboter) with the following steps:

TABLE.

| step | buffer | pH |
|---|---|---|
| equilibration | 25 mM Tris/25 mM NaCl | 7.4 |
| regeneration | 0.5 M NaOH | — |
| equilibration | 25 mM Tris/25 mM NaCl | 7.4 |
| charge | reaction mixture | — |
| wash 1* | 25 mM Tris/25 mM NaCl | 7.4 |
| wash 1 | 25 mM Tris/25 mM NaCl | 7.4 |
| wash 2 | 1M Tris/0.6 M NaCl | 7.4 |
| wash 3 | 25 mM Tris/25 mM NaCl | 7.0 |
| elution/recovery | 10 mM citrate/NaOH | 3.2 |
| wash 4 | 25 mM Tris/25 mM NaCl | 7.4 |
| regeneration | 0.5M NaOH | — |
| equilibration | 25 mM Tris/25 mM NaCl | 7.4 |
| storage | 200 mM benzyl alcohol/ 10 mM sodium acetate | 5.0 |

After the removal of β-Galactosidase the pH-value was set to pH 5.0+/−0.2 with Tris-HCl pH 9.0. The concentration after purification was measured with a photometer.

Enzymatic Reaction:
For about 1000 µg antibody about 50 µl (0.5 U) neuraminidase was added. The samples were incubated at about 37° C. for about 18 hours.

Results:
After the incubation with the enzyme the enzymatically modified antibody was obtained with a yield as depicted in the following table.

TABLE

| antibody before reaction | antibody after reaction | G1 [%] | other glycostructures |
|---|---|---|---|
| anti-CD19 antibody G1-NANA glycostructure | anti-CD19 antibody G1 glycostructure | >75 | Mannose 5 G1-Fuc G2 G1-GlcNac |
| anti-CCR5 antibody G1-NANA glycostructure | anti-CCR5 antibody G1 glycostructure | >65 | Mannose 5 (approx. 20%) G1-Fuc G1-GlcNac |
| anti-HER2 antibody G1-NANA glycostructure | anti-HER2 antibody G1 glycostructure | >80 | G1-GlcNac (approx. 10%) G1-Fuc G0 |
| anti-IL1R antibody G1-NANA glycostructure | anti-IL1R antibody G1 glycostructure | 80-90 | G2 (10-15%) |

It has to be pointed out that the obtainable yield of the G1 glycostructure depends beside the enzymatic conversion also on the glycostructures purity of the starting product. Thus, the presence of glycostructures such as Mannose 5, G0-GlcNac, G1-GlcNac, G0-Fuc, G1-Fuc, G2-Fuc and others reduces the obtainable yield as these glycostructures cannot be converted.

The invention claimed is:

1. A method for producing an immunoglobulin or immunoglobulin fragment or immunoglobulin fusion, having a G1 glycostructure, comprising the following steps:
    incubating an affinity chromatography column eluate containing the immunoglobulin or immunoglobulin fragment or immunoglobulin fusion with a galactosyltransferase to obtain a galactosyltransferase reaction product,
    incubating the galactosyltransferase reaction product with a sialyltransferase to obtain a sialyltransferase reaction product,
    incubating the sialyltransferase reaction product with a beta-1,4-galactosidase to obtain a beta-1,4-galactosidase reaction product,
    removing or inactivating the beta-1,4-galactosidase, and
    incubating the beta-1,4-galactosidase reaction product, in which the beta-1,4-galactosidase has been removed or inactivated, with a sialidase and thereby producing the immunoglobulin or immunoglobulin fragment or immunoglobulin fusion with the G1 glycostructure.

2. The method according to claim 1, wherein the galactosyltransferase is added during the incubating step in two or more aliquots.

3. The method according to claim 1, wherein the galactosyltransferase is added during the incubating step in three to six aliquots.

4. The method according to claim 2, wherein a first aliquot of the galactosyltransferase is added after zero to two hours incubation time.

5. The method according to claim 3, wherein a first aliquot of the galactosyltransferase is added after zero to two hours incubation time.

6. The method according to claim 4, wherein a subsequent aliquot of the galactosyltransferase is added after six to twelve hours incubation time.

7. The method according to claim 5, wherein a subsequent aliquot of the galactosyltransferase is added after six to twelve hours incubation time.

* * * * *